US00PP16817P3

(12) United States Plant Patent
Benardella

(10) Patent No.: US PP16,817 P3
(45) Date of Patent: Jul. 18, 2006

(54) MINIATURE ROSE PLANT NAMED 'BENPICO'

(50) Latin Name: *Rosa hybrida 'minima'*
Varietal Denomination: BENpico

(75) Inventor: Frank A. Benardella, Englishtown, MA (US)

(73) Assignee: Nor'East Miniature Roses, Arroyo Grande, CA (US)

( * ) Notice: Subject to any disclaimer, the term of this patent is extended or adjusted under 35 U.S.C. 154(b) by 41 days.

(21) Appl. No.: 10/857,788

(22) Filed: May 28, 2004

(65) Prior Publication Data

US 2005/0268363 P1 Dec. 1, 2005

(51) Int. Cl.
*A01H 5/00* (2006.01)

(52) U.S. Cl. ..... Plt./116

(58) Field of Classification Search ..... Plt./116
See application file for complete search history.

*Primary Examiner*—Anne Marie Grunberg
*Assistant Examiner*—Annette H Para

(57) ABSTRACT

'BENpico' is a new and distinct variety of miniature rose plant primarily identified by its pure white flowers edged with dark red and its miniature hybrid tea flower form. Blooms are borne singly and in small clusters on long straight stems, good for cutting and ideal for exhibition. When in bloom the plant makes an outstanding, decorative perennial in the ground or in containers. Its semi glossy foliage offers good disease resistance in all areas of the Mainland United States.

1 Drawing Sheet

CROSS REFERENCE

This new invention bears resemblance to 'BENmagic' (U.S. Plant Pat. No. 8,603) BENmagic is the grandparent of this new invention on the pollen parent side, and from the same breeding program. The pollen parent of this new invention is 'BENmjul' (U.S. patent application Ser. No. 10/035,940, abandoned). The pollen parent of 'BENmjul' is 'BENmagic'.

Similarities: The flowers of both plants have similar coloring. 'BENmagic' has white petals edged with a truer red and the new invention; 'BENpico' has white petals edged in a pinker-red. Markings on the petals are similar in the way the colors feather together.

Differences: The flowers of 'BENmagic' rarely open completely to expose the stamens, which lends it to a smaller open bloom size. However, the flowers of this new invention are actually smaller, which can be noted from bud size to depth of open bloom. Further, BENmagic has thicker flower petals and thicker and glossy foliage compared to the semi-glossy to matte foliage on this new invention. The plant habits are also noticeably different with the new invention being more branched and more vigorous and with smaller foliage then 'BENmagic'.

RIGHTS TO THE INVENTION

Be it known that Frank Benardella of Englishtown, N.J., claims invention of new and useful improvements in Rose Plant/var. 'BENpico' and following is a clear and exact description of the same.

Genus and species: *Rosa hybrida 'minima'*.

Varietal denomination: 'BENpico'.

BACKGROUND OF THE INVENTION

This present invention relates to a new and distinct variety of hardy, bush type plant of the miniature rose class. This new variety was created in a greenhouse in Englishtown, N.J., by crossing the following two rose plants:

The seed parent is an unnamed, unintroduced red and white seedling, from this same breeding program.

The pollen parent is 'BENmjul' (U.S. patent application Ser. No. 10/035,940, abandoned).

The primary goal of this breeding program is to produce unique roses with award winning hybrid tea form on comparable plants and with public appeal. To achieve this goal, roses are selected for this hybridizing program primarily for their award winning hybrid tea form.

How that relates to the new rose: The seed parent and the pollen parent are both roses bred by the inventor and have exhibition hybrid tea flower form. The pollen parent is a miniature rose plant with blooms of hybrid tea form in a miniature size, which went on to be introduced for sale to the public. The seed parent did have perfect hybrid tea flower form but the plant was not of desirable size. Hopes were to acquire its flower form only, which was successful in this cross.

This present invention bares resemblance to its pollen parent in the well-branched plant habit, the size and shape of the prickles and perhaps in the fact that the reverse of the petals of the pollen parent are flushed white.

Differences: The seed parent was overall a much larger and more sprawling plant and with larger blooms. The pollen parent has dark red petals with a flushed white reverse, the new invention has white petals with dark red edges; this new invention also has smaller buds and flowers each with more petals on a smaller & more compact plant.

Asexual reproduction by cuttings of this new variety in Rowley, Mass., Englishtown, N.J., and Arroyo Grande, Calif. shows that all distinguishing characteristics of this rose continually come true to form.

SUMMARY OF THE INVENTION

The present invention relates to a new and distinct variety of hardy, dwarf, bush-type rose plant of the miniature class with red and white flowers. The field of comparison with other red and white flowering miniatures is narrowed down to primarily those with red margins on white petals with a white reverse. This new invention is the only white miniature rose, of which I am aware, with this proportion of a dark purple-red along the edges that has white all the way to the base of the petals and including at attachment. This new variety is differentiated from other red and white flowering miniature roses with hybrid tea, exhibition-type blooms by its very white flowers edged in a deep purple-red, the red is noticeably darkest on the tips of the outer petals. The center petals and petaloides of this new invention occasionally do not unfurl but fade and fall as the rest of the petals. This new invention has adventitious foliage near the top of the flowering stem, not typical of all roses.

The variety is further characterized by:

Flowers that hold up well as cut flowers

An abundance of these flowers borne singly and in clusters

Mild fragrance

A uniformly branched plant with dark green, semi-glossy foliage

A plant that grows and blooms satisfactorily both in the greenhouse and outdoors, providing outstanding decoration in the garden as a perennial, in a border, or in large containers.

BRIEF DESCRIPTION OF THE DRAWING

The accompanying color photograph, taken in April, shows specimens of the buds, flowers and foliage of this new variety in different stages of development as grown under plastic in Arroyo Granda, Calif.

BOTANICAL DESCRIPTION OF THE PLANT

Following is a detailed description in outline form pertaining specifically to this new and distinct variety of miniature rose plant as observed at 1 year of age in a 6 inch standard nursery pot, grown indoors, under plastic in San Luis Bispo County, Calif., and a plant at 6 years of age growing in a 10 inch standard, nursery pot in Essex County, Mass. Observations of plant surfaces were made under and ×10 microscope, unless noted otherwise. All major color plate indentifications made are referring to The Royal Horticulture Society Chart except where common terms of color definition are employed.

FLOWERS

Genus/species: *Rosa hybrida minima*.

Varietal denomination: 'BENpico'.

Market class: Miniature Rose.

Blooming habit: Cyclic bloomer, having at least three long flushes of bloom each season.

Borne: Mostly in sprays of 3 or 4 and occasionally 5, but also often singly.

Bud: Size: just before the sepals divide, generally 15/32 of an inch in length measured from the top of the receptacle to the tip of the bud and 13/32 of an inch in diameter at the widest point.

*Form.*—Ovoid with an acuminate apex and truncate base.

*Color.*—The first color seen as the sepals begin to divide is a very dark red, near 53A, as the sepals continue to divide there will be streaks of near 53A where the sepals first opened and near 53C on either side of those darker streaks toward the base, a light green, near 145C.

Sepals: Color — outer surface (anthocyanin coloration present) near 144A, those sepals exposed to full sun are flushed with near 176A, which carries down onto that area of the receptacle to which it is attached inside surface — pilose, appearing near 147D, with ciliata appearing white, near 155D, and the adaxial surface of the sepal appendages and tips are the same as the outer surface, near 144A.

*Size.*—The outermost sepal extending 7/32 inch beyond the tip of the bud just before the sepals start to divide being a total length averaging 24/32 inch; most often having 2 or 4 foliaceous appendages on each side, and a lanceolate tip, up to 7/16 in length, with none to 7 small foliaceous appendages 2 innermost sepals — average 9/16 to 13/16 of an inch long to the very tip, with a subulate apex beginning 3/16 to 5/16 inch from the tip, and being 7/32 and 8/32 inch wide, with no appendages — margins are entire 2 sepals in between are between 23/32 and 25/32 inch long; their characteristics vary — they always have one margin with foliar appendages but the other margin may have the appendages or may be entire, their tips may be lanceolate, or acuminate.

*Other characteristics.*—There are glands on the tip of each sepal and on the tip of each foliar appendage; the margins are ciliate with a few stipate glands; outer surfaces have a few hairs and stipate glands; the inner surface is pilose; rolling back adjacent to the petals; after petal drop they begin to return to an upright position, remaining permanently attached to the receptacle.

Peduncle: Length — 1 to 1 5/16 inches.

*Aspect.*—Straight.

*Strength.*—Strong.

*Diameter.*—Most often 3/16 inch, occasionally 4/16 inch.

*Color.*—Yellow green, near 144A, and the neck or a portion of it oriented toward the sun may be flushed with 176A from the greyed-orange group, which may extend up onto the adjacent side of the receptacle.

*Texture.*—Glabrous.

*Appearance.*—Numerous glands, 2 to 4 stipate glands, and a very few single hairs; a several additional hairs are located just before the peduncle attaches to the stem.

Receptacle: Pitcher shaped.

*Size.*—7/32 inch diameter and 8/32 high.

*Color.*—Anthocyanin coloration present; near 143C, "Scheele's Green"; when exposed to full sun there may be an area flushed with the near 176A, sometimes only near the base, and sometimes extending onto an adjoining area of the sepal above or onto the peduncle below.

*Texture.*—Glabrous.

*Appearance.*—Semi glossy; may have 1 to 4 microscopic hairs.

*Top of receptacle.*—Shape — round. Color — a very light yellow-green, near 145C. Size — about 3/16 inch diameter. Surface — glabrous except for some hairs at the base of the styles, which are all set down in an alveola; the alveola is centered exactly in the top of the receptacle and has a diameter 1/16 inch.

Bloom: Size: When fully expanded — not symmetrical on the specimens studied: 1 5/16 by 1 8/16 inches across to 1 8/16 by 1 12/16, and near 3/4 inch deep; after petals fade the bloom expands to 1 11/16 by 1 13/16 inches across.

*Borne.*—In small clusters of 3 and occasionally 4 blooms per stem, and also singly.

*Form.*—Very high centered at first, a convex upper profile with a cupped lower profile; edges of outer petals begin rolling outward to a small degree as the bud opens and increasing as the blossom matures so when full open the outer petals take on a deltoid shape with cute apices; as blossoms fade upper profile becomes flattened convex and the lower profile becomes broader cupped; all petals continue to loosely roll back giving all the petals the appearance of having acute apices.

*Petalage.*—Under normal conditions — 26 to 32, ranging from 24 to 42 and with 3 to 13 petaloides, converse to expectations, the more petals per flower, the more petaloides.

*Fragrance.*—Mild.

*Persistence.*—8 to 12 days.

*Lasting quality as cut flower.*—6 to 10 days.

Petals: Texture: medium thickness; upper surfaces have stipate glands plus a few hairs near the base; there are glands along the margins; the outer surface has hairs at the base and along the primary vein, and occasionally around some secondary veins.

*Appearance.*—Inside — velvety, outside — satiny.

*Form.*—Obovoid.

*Apex.*—Rounded, emarginate.

*Base of the petals.*—Ovoid.

*Margin.*—Sinuate.

*Length and width.*—5/8 to 6/8 inch wide by 7/8 inch long.

*Arrangement.*—Imbricated.

*Persistence.*—Usually drop off cleanly in 10 to 14 days.

*Color.*—During the first few days — all petals of the flower except for the outer 8 to 10 petals are white, near 158D, and near 63A, Spiraea Red, along the margins and outer edges, gradually feathering about 1/3 of the way into the white, and near 158B a very light yellow at the point of attachment reverse is pure white, near 155D, with the color along the outer edges appearing near 57C, which seems to be the color from the upper surface showing through with the margin near 63A from the front, and at attachment is near 158B, outer 8 to 10 petals are white with just a hint of green, near 157D, and along the outer edges is darker than the inner petals, near 57A, "Tyrian Purple" and becoming lighter, 57B, "Rose Bengal", as it blends into the white and finally to 57C if it goes more than 1/3 of the way down the petal; along the outermost edge of the 5 outermost petals is an even deeper and redder color, near 53A, "Cardinal Red"; color at the point of attachment is near 157B, a slightly greenish-white reverse of the 8 to 10 outermost petals is near 155D, and the outer edges are also near 53A but coloration, near 61C, "Tyrian Purple", and sometimes with near 57B, often dips down towards the center of the reverse of the petals in a funnel shape; the 5 outermost petals additionally have darker coloring periodically going all the way to base which are different shades of red-purple, darker shades of near 59B or near 187D and occasionally 53A as well as lighter shades of near 63A, not the same on each petal and appears to be related to the orientation to the sun, near 158B at the point of attachment.

*Color when half blown, the colors lighten.*—The center petals, near 158D with near 57C from the margin feathering 1/3 of the way down the petal, and near 8D, a very light yellow, at attachment reverse is the same coloring as the upper surface except for appearing near 57D along the outer edges outer petals, near 157D, the margins and outer edges become darker, near 57A, feathering 1/3 of the way into the white, and near 157B, a very light green at attachment reverse is the same as the upper surface except appearing near 57D along the outer edges; on certain petals, near 57A dips down from the upper margin towards the center of the reverse of the petals in a funnel shape.

Color as the bloom ages, the main portion of the petals remains white, near 158D; on the upper surfaces, the margins of the outermost petals remain near 57A, only feathering 1/4 of the way down the petals and lightening some to 64B as it does so; the outermost edges of the outermost petals become darker to a color between 59B and 61A; the margins of the rest of the petals lighten to near 63B, "Spirea Red", and only going 1/5 of the way down the petal and with more of white showing in the feathering reverse of the outer petals also has a darker edge, near 59B, which also dips down towards the center of the reverse of those same petals in a funnel shape, and the rest becoming lighter, near 57D as it blends into the white.

Petaloids: The smallest ones being 5/16 inch long and as narrow as 1/8 inch; up to 5/8 inch long and 1/2 inch wide where only the crinkled margin differentiates them form a petal.

*Texture.*—Same as the petals.

*Form and margin.*—All have crinkled margins; those closest to the center of the flower are often emarginate; distortion increases toward the center of the flower, some being arched as much as 80° toward one side and about half appearing as a petal split down the middle.

*Color.*—The same as the outer petals (excluding the darker coloring along the outer edges of the outermost petals) even though they remain curled inward and are never exposed directly to light.

*Color just before the petals drop.*—The uppermost margins of the petaloides and of the innermost petals are near 64C, going 1/2 way down the petaloides but only 3/16 to 4/16 inch (1/4 to 1/5 of the way) down the innermost petals before it begins to blend in with the white, near 158D, which makes up the rest of the petal surface; the outermost edges of the 5 outermost petals are near 59C; the remainder of the outer edge is near 61C for 2/16 to 3/16 inch (about 1/5 of the petal) before beginning to blend into the white, near 157D; the rest of the petals are near 63C along the outer edges and downward for about 1/5 of the petal before it begins to blend into the white reverse of all the petals and petaloides is near 157B with the upper 1/3 to 1/2 being suffused lightly with near 60D, being darkest along the veins and the outermost petals still having the darker markings as before but now of near 59C at the point of attachment, both sides — near 158B.

*General tonality.*—Dark red and white after a couple of weeks: White with dark pink edges.

*General tonality from a distance.*—Dark pink and white.

REPRODUCTIVE ORGANS

Stamens, filaments and anthers:

*Arrangement.*—Perigynous —regularly arranged around styles.

*Quantity.*—About 56.

*Filaments.*—Length —5/32 to 8/32 inch, most often near 6/32 inch general color — white, near 155D.

*Anthers.*—Color — very pale orange-yellow, near 18D. Pollen color: a medium and soft shade of yellow-orange, near 19A. Quantity: small amount. Fertility: Fertile.

*Pistils, styles and stigmas.*—Quantity: 14 to 18. Styles: one bunch set in an alveola in the center of the receptacle; straight and of even length. Length: 1/8 inch long. Color — a very light yellow-green, all except close to the base is suffused lightly with near 52A.

*Stigmas.*—Color — near 158C from the yellow-white group.

Hips: There are no hips to observe at this time. The inventor of this new invention does recall having about 25 small hips per mature plant when artificially pollinated. Seeds are viable.

PLANT

Habit: Upright, very well branched.

Growth: Vigorous, uniformly branched.

*Height.*—18 to 24 inches.

*Width.*—16 to 20 inches.

*Distance between nodes.*—About 1¼ inch.

*Root initiation form cuttings.*—6–10 days.

*Length of flowering stem.*—4 to 6⅛ inches, most often about 5 inches.

Foliage: Pinnately compound; young plants will have mostly 5 leaflets and occasionally 3; mature plants, over 3 years of age will have mostly 7 leaflets and occasionally 3 and 5, especially bellow a flower bud or cluster.

*Quantity.*—Leaves are borne alternately and about 1¼ inches apart.

*Size of mature leaf.*—3¼ to 4¼ inches long when measured along the rachis from attachment at the stem to the apex of the terminal leaflet.

*Leaflets.*—Shape — ovate with an acute apex and most often an obtuse base (occasionally the base may be oblique). Size mature terminal leaflet — length — 1 5/16 to 1 15/16 inches from the base of the leaf to the apex, Width — at its widest point, ¾ to 1 inch relative to the length of the entire leaf. Color new foliage — anthocyanin coloration present upper surface — dark green, near 139A; the main and secondary veins are flushed with near 183B, "Oxblood Red", and the leaf margins all appear near 183B reverse — generally lighter in color: near 144A, variably flushed with near 184A of the greyed-purple group and the primary and secondary veins being near 184A. Color older foliage — anthocyanin coloring absent. upper surface — darker green, between 139A and 147A. reverse surface — a medium yellow-green, near 148B, and primary and secondary veins being a bit lighter, near 147C.

*Appearance.*—Upper surface on young foliage is semi glossy, as it ages it becomes matte reverse — matte with veins slightly protruding.

*Texture.*—Upper surface is seemingly glabrous, having just a few hairs, ranging from very short to unusually long and each hair is located independently; when the plant matures, there may be 0 to 3 hairs on the entire leaflet surface reverse, coriaceous, with several single hairs randomly located, occasionally a few hairs will be located in the same proximity.

*Edge*—Serration — nearly even serration; on young foliage the tip of each serrate supports a single plant process, randomly: a gland with anthocyanin coloring, a gland with anthocyanin coloring absent, a stipate gland without coloring or a single hair; as the foliage matures, all glands take on anthocyanin coloring, and their may be a few additional single hairs randomly along the margin and also on the adaxial leaf surface.

Petiole: Size — diameter, averaging 1/16 inch.

*Color on young leaf.*—Upper surface — near 183B, "Oxblood Red" along the ridges and near 146C, a medium olive-green, flushed with near 183B in the groove reverse — a light pea soup green, near 152D flushed with 184A of the greyed-purple group.

*Color on old leaf.*—Upper surface near 147C in the groove and deeper green, near 139A, along the ridges reverse — near 146A.

*Texture.*—Upper surface, a few to several hairs in the grove with more concentrated where the petiolules are connected; stipate glands sparsely line the ridges in varying numbers with more at the point where the basil leaflets are attached under side, glabrous.

*Size.*—Ranges from 11/16 inch to 1 3/16 inches; diameter is usually 2/32 inch near the basil leaflets and from that point down the diameter gradually increases by 1/32 inch, flaring outward toward the attachment at the stem where it is about 3/32 inch in diameter.

Rachis: Color on young foliage — upper surface — near 183B along the ridges and near 146C in the groove under surface — a light pea soup green, near 152D very lightly flushed with near 183B.

*Texture.*—Same as the petiole, except there are 0 to 4 prickles.

*Size.*—Length on mature 7-leaflet leaf is most often 1 5/32 inches; diameter is between 2/32 and 3/32 inch.

Petiolules: Diameter — 3/64 inch.

*Length.*—To the terminal leaflet is usually ½ inch long and about 1/32 to 2/32 inch long to the remaining leaflets.

*Color on young leaf.*—Upper side, near 184C. reverse — near 183D.

*Color on old leaf.*—Upper surface near 146D, a medium olive-green and continuing up the primary vein and secondary veins to ⅓ to ½ of the way up the leaflet reverse — lighter and with less olive coloration, near 147D.

*Texture.*—Glabrous, both adaxial and abaxial surface.

Stipules: One attached on each side of the base of each petiole at the plant stem.

*Size.*—On mature leaf, one usually being 3/64 of an inch longer than the other as uneven pairs, attached to the petiole for 16/64 and 19/64 inch to 20/64 and 23/64 inch and then each curving out at about a 45° angle usually for 10/64 inch (may be as short as 8/64 inch); width is between 2/64 and 3/64 inch, running parallel to the petiole to which it is attached. Margin is sinuate; stipules stand straight out perpendicular to the petiole for the fist 5 weeks or more and the detached tips point upward (adaxil); the edges of the attached portion of the stipules curl back as the leaf ages and the detached tips then become on a plane parallel to the petiole.

*Edge.*—Unevenly serrated; the tip of nearly every serrate has a stipate gland — only a couple or few serratures near the apices may have no gland.

*Color.*—Adaxial surface, lettuce green, near 144C and the veins appearing slightly lighter, near 144D; along the edge that is curled back is a much deeper green, near 137A, reverse is lighter, near 144C and near 137C, respectively.

*Texture.*—Upper surface is glabrous and glossy, under surface is matte.

Other information about the foliage: At the base of each peduncle is a small simple leaflet-like foliar appendage or there may also be one opposite, attached to the base of the peduncle by a petiole; the shape of the appendage is ovate-lanceolate; size ranges from about 1 inch to up to 1⅜ inches long with a petiole of about ⅜ inch long and averaging ⅜ inch wide when below a singly borne bud and ½ inch up to 11/16 inch long with a petiole of about ¼ inch in length and averaging 3/16 inch wide when below a bud in a cluster; the serration of the margin is more pronounced then that of the leaflets; there are stipules completely attached opposite at the base of these petioles; below the peduncle and near the end of the flowering stem are 1 or 2 adventitiously located simple leaflets, sometimes having a very pronounced serrated margin and being up to the size and shape of the basil leaflets and sometimes being bi- or tri-lobed, of average length comparable to that of the terminal leaflets and 1 to 2 times wider than the terminal leaflets and each attached with a petiole and having stipules closely resembling those of the leaves.

Resistance: Above average resistance to mildew and blackspot; no rust observed; good resistance to insects.

Wood: Appearance — there are 18 to 24 nearly parallel, vertical rows of stomata the entire length of every stem surface on both new and old growth, which are clearly visible under a ×3 microscope; there are new rows starting and stopping as they progress down the stem but the total number of rows remains about the same.

*New wood.*—Color — near 147B yellowish green. Texture — glabrous, Appearance — only a random few hairs.

*Old wood.*—Color — near 144B; older may become corky, near 177D. Texture — coarse. Appearance — the areas of cork cambium do not completely cover the old wood but do appear along the rows of stomata usually after the 5th or 6th year; there are only 4 to 7 lenticular shaped lenticels per inch of stem, with 3 or 4 often contiguous; lenticels are visible at ×3 or stronger.

*Diameter.*—Main stalks — avg. ½ inch; primary laterals, between 5/16 and 6/16 inch; secondary laterals, 3/16 to 4/16 inch; flowering stem, 2/16 inch.

Prickles: 1 or 2 located in the area immediately below each node and one in between nodes.

*Form.*—A flat, elliptical base tapering to a fine point; straight or slightly curved down.

*Length.*—3/16"; the base of the thorn is elliptical and about 3/16" inch in length.

*Quantity on main stalks.*—¾ inch from base on the main stalks is a section 1" long with 5 to 7 prickles, (no other section of the main stalks have this many prickles), decreasing to 3 to 4 per inch on laterals, 3 to 4 per inch of stem on flowering stems, 2 to 3 per inch on candelabra growth (that growth which shoots up quickly from the base of the plant to above the crown of the plant, caused by extreme changes of temperature between night and day of usually more than 30° Fahrenheit) — there are 1 or no prickles for up to the first 5 inches; distance between nodes is 2¼ to 2⅞" as compared to the 1" between nodes on the laterals and in both cases the location and quantity of prickles in relation to the nodes is the same.

*Color.*—When young, near 185B, "*Chrysanthemum* Crimson"; as it matures, becoming near 199C, from the greyed-brown group, and flushed on at least one side with near 185B; then becoming, near 177B, an orange-brown, and becoming darker when old, near 177A.

*On leaves.*—Underside of the rachis/petiole 0 to 4. Size — 2/16 inch long. Color — rather translucent, near 153D, a dull greenish-yellow.

Hardiness: Tested winter hardy in zones 4 through 9, winter protection recommended for zones 6 and colder; and heat tolerant in Horticultural Society heat zones 9 through 1. It is claimed:

1. A new and distinct variety of hardy, miniature rose plant is claimed, substantially as illustrated and described, with hybrid tea form flowers of pure white with a vivid red edging born on long straight stems, dark green semi glossy foliage with good disease resistance and anthocyanin coloring present in young growth.

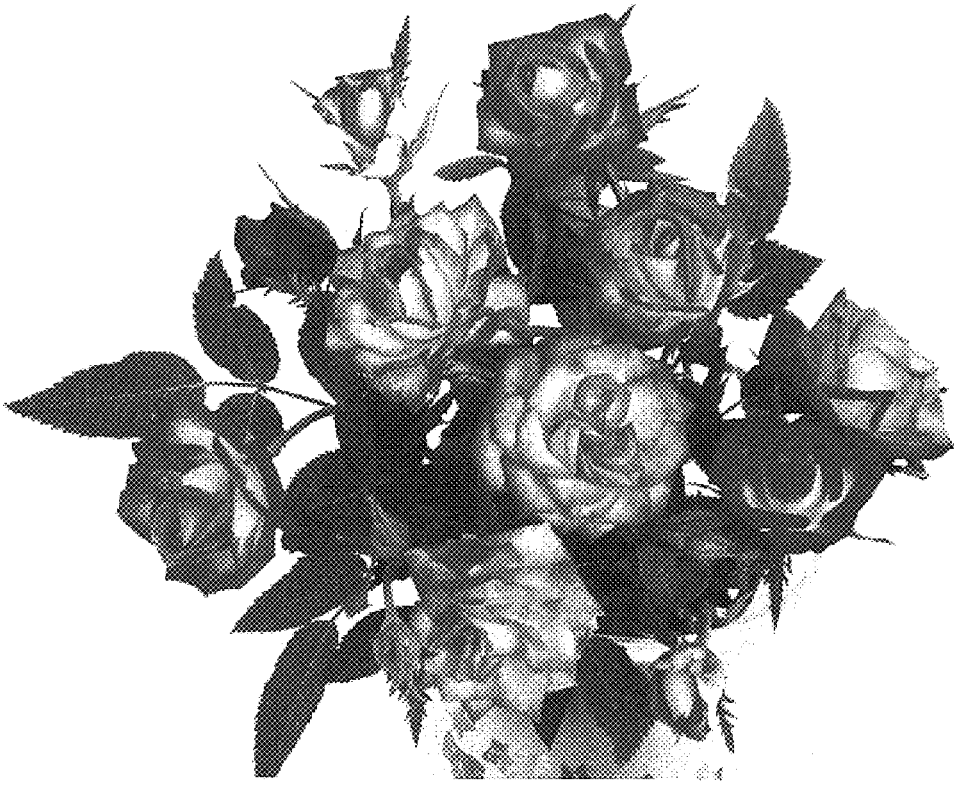

* * * * *